US007968128B2

(12) United States Patent
Xie et al.

(10) Patent No.: US 7,968,128 B2
(45) Date of Patent: Jun. 28, 2011

(54) PLANT EXTRACT COMPOSITIONS FOR AFFECTING SLEEP

(75) Inventors: Xueji Xie, Richmond (CA); Yu-Lung Ko, Richmond (CA); Chien-Kuang Ko, Richmond (CA); Jason Jiang-Chung Ko, Richmond (CA); Richard William Gafney, Richmond (CA)

(73) Assignee: VIVA Pharmaceutical Inc., Richmond, British Columbia (CA)

( * ) Notice: Subject to any disclaimer, the term of this patent is extended or adjusted under 35 U.S.C. 154(b) by 0 days.

(21) Appl. No.: 12/263,868

(22) Filed: Nov. 3, 2008

(65) Prior Publication Data

US 2010/0112107 A1 May 6, 2010

(51) Int. Cl.
*A61K 36/00* (2006.01)
(52) U.S. Cl. .......................................... 424/725; 424/769
(58) Field of Classification Search .................... None
See application file for complete search history.

(56) References Cited

U.S. PATENT DOCUMENTS

| 5,992,421 | A * | 11/1999 | Bae ............................. | 131/369 |
| 2002/0009506 | A1* | 1/2002 | Tao ............................. | 424/728 |
| 2005/0142223 | A1* | 6/2005 | Gong et al. .................. | 424/728 |
| 2005/0142230 | A1 | 6/2005 | Gong et al. | |
| 2006/0198872 | A1* | 9/2006 | Ikonte et al. ................. | 424/439 |
| 2008/0118583 | A1* | 5/2008 | Olalde Rangel ............. | 424/728 |
| 2008/0254071 | A1* | 10/2008 | Taraborrelli et al. ........ | 424/275.1 |

FOREIGN PATENT DOCUMENTS

| CN | 1513516 | * | 7/2004 |
| CN | 1513516 | A | 7/2004 |
| CN | 1748774 | * | 3/2006 |
| CN | 1748774 | A | 3/2006 |
| CN | 1765390 | * | 5/2006 |
| CN | 1765390 | A | 5/2006 |
| CN | 1814072 | * | 6/2006 |
| CN | 1814072 | A | 8/2006 |
| CN | 1824128 | * | 8/2006 |
| CN | 1824128 | A | 8/2006 |
| CN | 1973889 | * | 6/2007 |
| CN | 1973889 | A | 6/2007 |
| CN | 1513516 | | 7/2007 |
| CN | 100998664 | * | 7/2007 |
| CN | 100998664 | A | 7/2007 |
| CN | 10109980 | * | 8/2007 |
| CN | 101011537 | * | 8/2007 |
| CN | 101011537 | A | 8/2007 |
| CN | 101011549 | * | 8/2007 |
| CN | 101011549 | A | 8/2007 |
| CN | 101019980 | A | 8/2007 |
| CN | 101020022 | * | 8/2007 |
| CN | 101020022 | A | 8/2007 |
| CN | 101040964 | * | 9/2007 |
| CN | 101040964 | A | 9/2007 |
| CN | 101053433 | * | 10/2007 |
| CN | 101053433 | A | 10/2007 |
| CN | 101057946 | * | 10/2007 |
| CN | 101057946 | A | 10/2007 |

OTHER PUBLICATIONS

Chuan Xia, et al. "The influence of spine date seed oil and platycladi seed oil on the active movements of mice by orthogonal design", Department of Pharmacology, School of Medicine, Xi'an Jiaotong University, p. 67, Apr. 2006, (see English Abstract).
"Study on the synergistic effect of Polygala tenuifolia and Ziziphus jujube seed in combination", Japanese Pharmaceutical Association 122th Annual Conference, p. 246 (see Translated English Abstract), 2002.
Wing Y.K., Hong Kong Medical Journal, vol. 7, No. 4, pp. 392-402, Dec. 2001.
Dharmananda S., "Tianwang Buxin Dan", Aug. 2001, URL: http://www.itmonline.org/arts/tianwang.htm Retrieved: Jan. 12, 2010.
Zhu J.X., et al., "Effects of Biota Orientalis extracts and its flavonoid constituents, quercetin and rutin on serum uric acid levels in oxonate-induced mice and xanthine dehydrogenase and xanthine oxidase activities in mouse liver", Journal of Ethnopharmacology, vol. 93, pp. 133-140, Mar. 26, 2004.
Chen J.K., Chinese Medical Herbology and Pharmacology, L. Crampton ed., Art of Medicine Press, City of Industry CA. USA., ISBN: 0-9740635-0-9, 2005 see Chapter 5, pp. 11-14, "Preparation and Processing of Chinese Herbs". see Chapter 14, pp. 751-776, "Shen-Calming Herbs".
International Search Report for PCT/CA2009/001600, mailed Feb. 8, 2010.
Written Opinion of the International Searching Authority for PCT/CA2009/001600, mailed Feb. 8, 2010.

* cited by examiner

*Primary Examiner* — Christopher R. Tate
(74) *Attorney, Agent, or Firm* — Larson & Anderson, LLC

(57) ABSTRACT

A composition for affecting physiological sleep disorders comprising a therapeutically effective amount of Baiziren extract or any of its derivatives, and a pharmaceutically acceptable carrier. The composition may additionally comprise a therapeutically effective amount of at least one of a Suanzaoren extract and a Yuanzhi extract, or mixtures thereof.

13 Claims, No Drawings

 US 7,968,128 B2 …

PLANT EXTRACT COMPOSITIONS FOR AFFECTING SLEEP

FIELD OF THE INVENTION

The present invention generally relates to plant extracts and in particular, to the use of plant extracts for modulating sleep disorders.

BACKGROUND OF THE INVENTION

A sleep disorder is typically classified as a medical disorder of the sleep patterns of a person or animal. In some cases sleep disorders are serious enough to interfere with normal physical, mental and emotional functioning. Sleep disorders may include dysomnias, insomnia, circadian rhythm sleep disorders, hypersomnia and parasomnias.

Insomnia i.e., sleeplessness is a common medical condition generally caused by over stimulation of the mind and/or body. Factors such as stress, poor dietary habits, lack of physical activity, pain, environmental factors and psychological factors are major causes of insomnia. The inability to sleep, poor-quality of sleep, and night waking can be a significant problem, sleep is necessary for both survival and good health. Sleep disorders can also lead to problems during the day for example, fatigue, difficulty in thinking clearly and/or staying focused, and feeling depressed and/or irritable.

How long a person sleeps and how rested a person feels on waking can be influenced by many factors, including excitement, physical exertion, and emotional distress as well as medications, food elements, and food additives.

When sleep disorders interfere with a person's normal activities, the intermittent use of sleep medications may be useful. Modern sleeping drugs are generally available as over-the-counter medications and are one of the more commonly used drugs on the market. However, many of the currently available sleeping pills, particularly hypnotics and sedatives should not be taken over extended periods of time. Continued long-term use may cause a person to build up a tolerance to the drug, and in addition may worsen the original sleep disorder, facilitate addiction, and cause withdrawal symptoms on discontinuing use. In addition, common side effects of currently available sleep medications may include inhibition of the muscle coordination system, central nervous system, and general functional abilities such as shuffling walk; tremor, inability to still or irregular heartbeat.

Sleep is vital to a healthy lifestyle. There exists a need to provide compositions for and methods of treating insomnia or sleeplessness that have fewer side effects.

Further, there is a need for compositions comprising natural, plant-based ingredients, that are generally non-addictive, have limited side-effects, and are not known to cause physiological withdrawal symptoms when use is discontinued.

BRIEF SUMMARY OF THE INVENTION

Exemplary embodiments of the present invention relate to compositions comprising certain selected plant extracts for therapeutic treatment and modulation of insomnia and/or sleeplessness. Other exemplary embodiments of the present invention relate to methods for making the compositions comprising the selected plant extracts.

An exemplary embodiment of the present invention relates to a composition comprising a therapeutic amount of a Baiziren extract. The composition may additionally comprise a therapeutic amount of a Yuanzhi extract, a therapeutically effective amount of a Suanzaoren extract, or mixtures thereof.

Another exemplary embodiment of the present invention relates to methods for preparing extracts from each of Baiziren, Yuanzhi, and Suanzaoren, and blending two or more of the extracts to provide one of said compositions.

DETAILED DESCRIPTION OF THE INVENTION

The terminology "treating insomnia" or "treating sleeplessness" used herein, unless otherwise specified, includes but is not limited to preventing or reducing disturbances in falling asleep, increasing the ability to remain asleep, reducing awakenings during sleep, increasing the duration and quality of sleep, and reducing abnormal sleep behaviours.

Surprisingly, it has been found that compositions comprising Baiziren extract alone, and in combination with at least one of Yuanzhi extract and Suanzaoren extract are useful for modulation of sleep disorders, e.g., insomnia. It has also been found that the compositions are useful for reducing the time needed to fall asleep and further, improve the quality of sleep. Unexpectedly, compositions comprising Baiziren extract, and novel combinations of Baiziren extract and at least one of Yuanzhi extract and Suanzaoren extract, are also useful for modulating memory loss, e.g., amnesia.

Baiziren extracts may be produced from dry seeds, leaves, stems and roots of *Platycladus orientalis*. According to one exemplary embodiment, Baiziren extracts are derived from one or more of *Platycladus orientalis* (L.) Franco leaves, seeds, and roots. The extracts may be derived directly from whole seeds. Alternatively, the seeds may be ground into powder, which is then heated to a temperature selected from a range of about 35 to 50° C., to remove oils prior to proceeding with the extraction steps which are explained in more detail below. According to one aspect, the Baiziren extract is derived from about 2 g to 15 g of dry seeds, leaves, and/or roots. In a further exemplary embodiment, Baiziren extract is derived from dry seeds of *Platycladus orientalis* (L.) Franco.

Suanzaoren extracts may be produced from the leaves, fruits and seeds of *Zizyphus jujuba*. Members of the *Zizyphus juuba* family include *Ziziphus jujube* Mill. Var. *spinosa* (Bunge) Hu ex H. F. Chou. In particular, the extracts are derived from about 5 g to 18 g of one or more of dry seeds, leaves, stems, fruits and roots. In one exemplary embodiment, Suanzaoren extracts are produced from *Ziziphus jujube* seed.

Yuanzhi extracts may be produced from one or more of the leaves, stems, and roots of *Polygala* spp. In particular, the extracts are derived from about 2 g to 15 g of dry seeds, leaves, and/or roots. It is optional for the Yuanzhi extracts to be derived from one or more of *Polygala tenuifolia* Wild, *P. sibirica* L. *P. sibirica* var. *megalopha* Franch., *P. japonica* Houtt., *P. hybrida* DC, *P. arillata* Buch.-Ham ex D. Don, *P. glomerata* Lour., *P. arvensis* Wild., *P. tatarinowii*, *P. fallax* Hemsl., *P. wattersii* Hance, *P. hongkongesis* var. *stenophylla*, *P. senega* L., and combinations thereof. Alternatively, the Yuanzhi extracts may be derived from one or both of *P. tenuifolia* wild or *P. sibirica* L., preferably from the dry roots of *P. tenuifolia* wild or/or *P. sibirica* L.

Another exemplary embodiment relates to compositions comprising Baiziren extracts, and Baiziren extracts in combination at least one of Yuanzhi extract(s) and Suanzaoren extract(s). These compositions are useful for modulating sleep disorders and particular, insomnia.

Other exemplary embodiments of the invention relate to methods for producing plant extracts from Baiziren, Yuanzhi, and Suanzaoren plant components. The extracts may be obtained from one or more plant components selected from the group comprising leaves, stems, roots, and seeds. Alternatively, the extracts may be prepared from whole plants. The extracts may be prepared from fresh or dried plants and plant components, and from mixtures thereof. The methods generally comprise the steps of:

(a) soaking the selected plants and/or plant components in an aqueous solvent at ambient room temperatures for a period of time selected from the range of about 15 minutes to about twenty four hours to produce an extraction mixture. Heat (e.g., from a range of above the ambient room temperature to about 110° C.) may be optionally applied during the soaking period. A suitable aqueous solvent is water. The aqueous solvent may additionally comprise one or more organic solvents exemplified by ethanol, methanol, isopropyl alcohol, ethyl acetate, hexane, acetic acid, and mixtures thereof. It is optional for the aqueous solvent to comprise an inorganic acid or base, alone or in combination with one or more selected organic solvents. It is also optional for the aqueous solvent to be intermixed and commingled with the plants and/or plant components during the soaking time period. If heat is not applied during the soaking time period, then it is suitable to heat the aqueous solvent and plant mixtures to above boiling for a period of time ranging from about 15 minutes to about two hours, to produce an extraction mixture;

(b) filtering the extraction mixture through a filter to produce an aqueous filtrate;

(c) collecting the aqueous filtrate; and (d) concentrating, i.e. de-watering the aqueous filtrate to at least a syrup-like consistency, and optionally, de-watering further to reduce the filtrate to a semisolid consistency. The methods may optionally include additional steps for drying the aqueous filtrates to powders.

The extractions may also be performed using methods known in the art, including decoction. The crude extracts may optionally be further purified using suitable chromatography columns, for example, silica gel and Sephadex LH-20. Alternatively, the plant materials may be extracted using super critical carbon dioxide equipment and procedures.

The Baiziren extract is optionally encapsulated in a softgel or hard capsule for oral ingestion. Alternatively, the Baiziren extract may be commingled and intermixed with one or more suitable carriers and/or excipients to produce a mixture which is formed into tablets. It is within the scope of the present invention to intermix and commingle the Baiziren extract with one or more of the Yuanzhi extract and Suanzaoren extract prior to the preparation of capsulation or tablets.

The following Examples illustrate exemplary compositions and methods of the present invention. It is to be understood these examples should not be considered as limitations, and that the experimental data are provided only for the purposes of illustration.

EXAMPLES

The following examples evaluate the effects of the Baiziren, Yuanzhi, and Suanzaoren extract compositions of the present invention, in comparisons to tests comprising hypnosis induced by sodium barbital sleeping times, side effects on locomotor activity, traction test, and inclined plane test in mice.

Animals:

Male and female Swiss mice having weights between about 18 to 22 g were used in the Examples provided below. Mice were housed in groups of 10 mice in a breeding room having a controlled temperature of about 22±2° C. Each group had free access to standard diet pellets and tap water.

Example 1

Preparation of Extracts

Baiziren extracts: Baiziren seeds (*Platycladus orientalis* (L.) Franco) were soaked in water in a ratio of 1:10 of seeds to water (w/w) for about 30 minutes, and then cooked at a temperature from a range of about 40° C. to 100° C. for about 40 minutes. The cooked mixture was filtered through Whatman #4 filter paper, and the aqueous filtrate was collected. The aqueous filtrate was concentrated by evaporation, and then dried to a powder using a vacuum pump. The dried Baiziren powder was labelled as 'A'.

Yuanzhi extracts: Dried *Polygala tenuifolia* Wild, and *P. sibirica* L. roots were soaked together in water in a ratio of 1:10 of root to water (w/w) for about 30 minutes, and then cooked for about 1 hour at temperatures ranging between 40° C. to 100° C. The cooked mixture was then filtered through Whatman #4 filter paper, and the aqueous filtrate was, collected. The aqueous filtrate was concentrated by evaporation and then dried to a powder using a vacuum pump. The dried Yuanzhi powder was labelled as 'B'.

Suanzaoren extract: Dried *Ziziphus jujube* seeds were soaked in water in a ratio of 1:10 of seed to water (w/w) for about 30 minutes, and then cooked for about 40 minutes at temperatures ranging between 40° C. to 100° C. The cooked mixture was filtered through Whatman #4 filter paper, and the aqueous filtrate was collected. The aqueous filtrate was concentrated by evaporation, and then dried to a powder using a vacuum pump. The dried Suanzaoren powder was labelled as 'C'.

Combinations of the extract powders were prepared in the following weight to weight ratios and were labelled "BS" and "BY", respectively:

| Extract Powder | Combination "BS" | Combination "BY" |
|---|---|---|
| Powder A | 1 | 0 |
| Powder B | 0 | 1 |
| Powder C | 3.64 | 2.48 |

Example 2

Drug and Extract Administration Protocol

Each of the extract combinations "BS" and "BY" produced in Example 1, was prepared for oral administration (PO) by ultrasonically dispersing each extract in distilled water containing about 0.5% Tween-80. Diazepam was also prepared for administration by ultrasonically dispersing the Diazepam in distilled water containing about 0.5% Tween-80.

Each of the BY, BS, and Diazepam compositions was administered orally to separate groups of mice at a dosage of 10 mL/kg body weight.

Each animal in the control groups in Examples 3 through 5 received a corresponding dosage of sterile distilled water.

Dosages of the BS, BY, Diazepam compositions, and the sterile distilled water were administered orally to groups of mice, wherein each group comprised at least 10 mice.

Example 3

Sodium Barbital Induced Sleep Time Measurement

Mice were administered 90 mg/kg sodium barbital via intraperitoneal injection (ip). Mice were then positioned on their back. The time that elapsed between administration of the sodium barbital and when each animal lost their righting reflex represented the time period between latency to the onset of sleep. The BS, BY, Diazepam, and the control treatments were administered to separate groups of mice. Each group of mice received their treatment about 7 days prior to the administration of the sodium barbital. The duration of sleeping time was calculated as the time interval between the loss of righting reflex to the time of recovery of this reflex. In studying the effects of the BS and BY extracts, the comparison of the durations of sleeping time between mice receiving the BS, BY, Diazepam treatments and the control treatments, was used as the main criterion of measurement. Table 1 below shows the effects of the BS and BY treatments on the durations of sleeping time.

TABLE 1

Effects of BS and BY compositions on sodium barbital-induced sleeping time test in mice (mean ± SE, n = 10)

| Group | Dose (g/kg) | Sleep latency (seconds) | Duration of Sleep (minutes) |
|---|---|---|---|
| Control | n/a | 230.3 ± 6.7 | 33.5 ± 4.1 |
| Diazepam | 1.0 mg/kg | 169.1 ± 12.4** | 72.8 ± 7.5** |
| BS | 0.8 | 233.1 ± 10.2 | 32.6 ± 3.6 |
|  | 1.6 | 227.8 ± 16.7 | 59.8 ± 10.9* |
|  | 3.2 | 226.9 ± 11.4 | 44.8 ± 6.6 |
|  | 6.4 | 235.6 ± 17.8 | 40.7 ± 5.0 |
| BY | 0.6 | 248.4 ± 23.5 | 31.0 ± 1.6 |
|  | 1.2 | 235.9 ± 21.8 | 64.8 ± 6.0** |
|  | 2.4 | 235.6 ± 12.3 | 65.0 ± 11.1* |

*significantly different (P < 0.05) from control (Student-t test).
**significantly different (P < 0.001) from control (Student-t test).

BS treatment at dosage 1.6 g/kg, and BY treatments at dosages 1.2 g/kg and 2.4 g/kg, and Diazepam treatment at dosage levels of 1.0 mg/kg, significantly prolonged the sodium barbital-induced sleeping time compared to the controls. Furthermore, based on statistical analyses using the Student-t test, each of Diazepam at a dosage of 1.0 mg/kg and BY at dosage of 1.2 g/kg significantly increased (P<0.001) sleeping times when compared to the controls, indicating that BY compositions may have similar hypnosis functions as Diazepam.

Example 4

Locomotor Activity Measurements

The effects of the BS treatments and the BY treatments on inhibition of central nervous system were evaluated by measurements of the locomotor activities of mice.

Each mouse was placed in the center of a square arena having dimensions of approximately 60 cm×60 cm×35 cm. The arena had a black floor which was divided into 16 equal squares using a white line. The arena was illuminated using red 25 W bulbs on the ceiling. The total number of squares each mouse entered in a 5 minute period was recorded by an overhead video camera. The camera was linked to a monitor and video recorder in an adjacent laboratory.

The locomotor activity of the mice were recorded both before and 30-minutes, 60-minutes, 120-minutes, and 180-minutes after administration of one of BS, BY, Diazepam, and the control.

All locomotor activity recordings were carried out with the observer unaware of the treatment that was administered to each of the mice.

TABLE 2

Effects of BS and BY compositions on locomotor activities in mice (mean ± SE, n = 10)

| | | Locomotor activity count | | | | |
|---|---|---|---|---|---|---|
| Group | Dose (g/kg) | 0 minutes | 30 minutes | 60 minutes | 120 minutes | 180 minutes |
| Control | n/a | 81.2 ± 9.0 | 62.3 ± 5.8 | 52.1 ± 4.1 | 47.1 ± 4.2 | 43.0 ± 5.0 |
| Diazepam | 1 mg/kg | 80.4 ± 6.7 | 68.9 ± 4.9 | 56.7 ± 3.8 | 52.6 ± 3.6 | 47.6 ± 3.4 |
| BS | 0.8 | 82.8 ± 8.7 | 61.5 ± 5.8 | 55.2 ± 4.2 | 48.1 ± 3.7 | 40.3 ± 4.5 |
|  | 1.6 | 83.4 ± 4.6 | 61.8 ± 4.7 | 49.9 ± 3.2 | 45.5 ± 4.9 | 41.0 ± 5.0 |
|  | 3.2 | 79.1 ± 8.1 | 62.5 ± 3.6 | 53.1 ± 4.1 | 49.9 ± 3.8 | 41.8 ± 5.7 |
|  | 6.4 | 81.3 ± 8.4 | 61.2 ± 6.4 | 52.6 ± 5.1 | 48.7 ± 3.8 | 42.7 ± 4.3 |
| BY | 0.6 | 80.3 ± 5.0 | 60.3 ± 4.5 | 52.2 ± 3.0 | 46.5 ± 1.6 | 39.5 ± 3.9 |
|  | 1.2 | 82.1 ± 9.3 | 62.7 ± 4.6 | 54.0 ± 4.5 | 46.4 ± 3.5 | 40.0 ± 2.8 |
|  | 2.4 | 80.1 ± 5.8 | 65.8 ± 3.3 | 50.9 ± 3.1 | 48.4 ± 2.4 | 40.3 ± 3.5 |

None of the BS, BY and Diazepam compositions had any significant effects on the locomotor activity of the mice indicating that there was little or no inhibition of central nervous system by any of the compositions comprising Baiziren, Yuanzhi, and/or Suanzaoren extracts.

Example 5

Traction Test

The effects of the BS and BY compositions on inhibition of muscle coordination systems were evaluated using a traction test.

A wire having a diameter of about 1.6 mm and length of about 30 cm was stretched and secured horizontally at a height of about 30 cm above a surface. Each mouse was placed such that the mouse was grasping the wire with all four paws. The duration of time each mouse clung to the wire was recorded up to a maximum of 60 seconds.

The test was performed about 60 minutes after the administration of one of the BS, BY, Diazepam, and the control compositions. The tests were performed in triplicate for each mouse. The durations of clinging time measured for each group of mice were calculated using the mean value of triplicates for each mouse. If the duration of clinging time was greater than 60 seconds, the mouse was released from the wire, and the clinging time was recorded 60 seconds.

TABLE 3

Effects of BS and BY on the Traction test in mice (mean ± SE, n = 10)

| Group | Dose (g/kg) | Duration of clinging (seconds) |
|---|---|---|
| Control | n/a | 53.8 ± 2.3 |
| Diazepam | 9 mg/kg | 19.6 ± 4.9** |
| BS | 0.8 | 55.8 ± 1.5 |
|  | 1.6 | 54.4 ± 2.7 |
|  | 3.2 | 50.0 ± 5.5 |
|  | 6.4 | 50.1 ± 4.4 |
| BY | 0.6 | 58.2 ± 1.1 |
|  | 1.2 | 56.9 ± 2.8 |
|  | 2.4 | 42.8 ± 6.4 |

**$P < 0.001$, compared with the control group

The durations of clinging time of the mice that were dosed with one of the BS and BY compositions, compared to mice administered the control treatment, were very similar. The data indicate that neither of the BS and BY compositions had significant effects on muscle coordination systems. Diazepam however, markedly reduced the duration of clinging time compared to the control group, indicating that Diazepam at least partially inhibited the muscle coordination system in mice.

Example 6

Inclined Plane Test

Effects of the BS and BY compositions on the motor functions of mice were evaluated using an inclined plane test.

The inclined plane consisted of two rectangular steel boards connected at one end by a hinge. One of the boards served as a base and the other as a movable inclined plane. Two protractor-like steel side panels with degrees marked on their faces were fixed to the base. A rubber mat with ridges of about 0.6 mm in height was fixed to the surface of the moveable plane. Mice were placed in such a position on the mat that their body axis was perpendicular to the axis of the inclined plane. The maximum inclination of the plane at which a mouse could maintain itself in position for at least 5 seconds was recorded, and interpreted to represent the mouse's functional ability. The test was performed in triplicate for each mouse and the mean value was recorded as the maximum inclination.

TABLE 4

Effects of the BS and BY compositions on the motor functions of mice as measured by the inclined plane test in mice (mean ± SE, n = 10)

| Group | dose (g/kg) | Maximum inclination (degrees) |
|---|---|---|
| Control | n/a | 64.7 ± 2.2 |
| Diazepam | 9 mg/kg | 51.5 ± 0.9** |
| BS | 0.8 | 65.7 ± 2.2 |
|  | 1.6 | 64.7 ± 2.2 |
|  | 3.2 | 66.0 ± 1.4 |
|  | 6.4 | 65.3 ± 1.7 |
| BY | 0.6 | 61.0 ± 0.9 |
|  | 1.2 | 65.4 ± 2.1 |
|  | 2.4 | 65.4 ± 0.9 |

**$P < 0.001$, compared with the control group

The degrees of inclination recorded for the mice that received dosages of one of the BS and BY compositions, compared to mice administered the control composition, were very similar. The data in Table 4 indicate that neither of the BS and BY compositions had a significant impact on the muscle coordination system of mice. Diazepam however, markedly reduced the maximum degree of inclination in comparison with the control group, which indicates that Diazepam at least partially inhibited the muscle coordination system in mice.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A composition for modulating physiological sleep disorders, said composition consisting of:
    (a) *Platycladus orientalis* extract;
    (b) a *Polygala* spp. extract;
    (c) optionally, a *Zizyphus jujube* extract; and
    (d) one or more pharmaceutically acceptable carriers or excipients, wherein the extracts are present in therapeutically effective amounts for modulating physiological sleep disorders.

2. A composition according to claim 1, wherein the *Platycladus orientalis* extract is prepared from at least one of a fresh plant component selected from the group consisting of seeds, leaves, stems, roots, flowers and fruits, and combinations thereof, and a dried plant component selected from the group consisting of seeds, leaves, stems, roots, flowers and fruits, and combinations thereof.

3. A composition according to claim 1, wherein the *Polygala* spp. extract is prepared from at least one of a fresh plant component selected from the group consisting of seeds, leaves, stems, roots, flowers and fruits, and combinations thereof, and a dried plant component selected from the group consisting of seeds, leaves, stems, roots, flowers and fruits, and combinations thereof.

4. A composition according to claim 1, wherein the composition includes a *Zizyphus jujube* extract and the *Zizyphus jujube* extract is prepared from at least one of a fresh plant component selected from the group consisting of seeds, leaves, stems, roots, flowers and fruits, and combinations thereof, and a dried plant component selected from the group consisting of seeds, leaves, stems, roots, flowers and fruits, and combinations thereof.

5. A composition of claim 1, wherein the physiological sleep disorder is selected from the group consisting of insomnia, parasomnia and combinations thereof.

6. A composition according to claim 1, wherein said composition is in a dosage form configured as one of a soft-gel capsule, a hard capsule, liquid, powder, and a tablet.

7. A composition according to claim 1, wherein said *Polygala* spp. extract and said *Platycladus orientalis* extract are present in a ratio between about 1:1 to about 2.4:1.

8. A method for producing a composition for modulating physiological sleep disorders, said method comprising the steps of:
   soaking a *Platycladus orientalis* plant component in an aqueous solvent at a temperature selected from the range of about 20° C. to about 110° C., thereby producing a *Platycladus orientalis* extraction mixture;
   soaking a plant component from *Polygala* spp. in an aqueous solvent at a temperature selected from the range of about 20° C. to about 110° C., thereby producing a *Polygala* extraction mixture;
   separating a liquid fraction from the *Platycladus orientalis* extraction mixture and from the *Polygala* extraction mixture;
   filtering said *Platycladus orientalis* liquid fraction to produce an aqueous *Platycladus orientalis* filtrate;
   filtering said *Polygala* liquid fraction to produce an aqueous *Polygala* filtrate;
   de-watering the aqueous *Platycladus orientalis* filtrate and de-watering the aqueous *Polygala* filtrate to at least a syrup-like consistency; and
   forming a composition consisting of said de-watered *Platycladus orientalis* filtrate, said de-watered *Polygala* second filtrate, and optionally a *Zizyphus jujube* de-watered filtrate, with one or more pharmaceutically acceptable carriers or excipients therefore.

9. A method according to claim 8, wherein the aqueous *Platycladus orientalis* filtrate and the aqueous *Polygala* filtrate are dewatered and processed to produce a dry powder.

10. A method according to claim 8, wherein the aqueous solvent comprises a mixture of water and at least one organic solvent selected from the group consisting of ethanol, methanol, isopropyl alcohol, ethyl acetate, hexane, acetic acid, and mixtures thereof.

11. A method according to claim 8, wherein the aqueous solvent comprises a mixture of water and at least one of an inorganic acid and an inorganic base.

12. A method according to claim 8, wherein said composition is configured as one of a soft-gel capsule, a hard capsule, liquid, powder and tablet.

13. A method according claim 8, wherein the *Zizyphus jujube* extract is present and is prepared by a method additionally comprising the steps of:
   soaking a plant component from *Zizyphus jujube* in an aqueous solvent at a temperature selected from the range of about 20° C. to about 110° C., thereby producing a *Zizyphus jujube* extraction mixture;
   separating a liquid fraction from the *Zizyphus jujube* extraction mixture; and
filtering said liquid fraction to produce an aqueous *Zizyphus jujube* filtrate; and
   de-watering the aqueous *Zizyphus jujube* filtrate to at least a syrup-like consistency.

\* \* \* \* \*

UNITED STATES PATENT AND TRADEMARK OFFICE
CERTIFICATE OF CORRECTION

PATENT NO.        : 7,968,128 B2
APPLICATION NO.   : 12/263868
DATED             : June 28, 2011
INVENTOR(S)       : Xie et al.

Page 1 of 1

It is certified that error appears in the above-identified patent and that said Letters Patent is hereby corrected as shown below:

Claim 8, Column 10, Lines 5-6 should read – ... *Platycladus orientalis* filtrate, said de-watered *Polygala* filtrate, and optionally a *Zizyphus jujube* de-watered...

Claim 13, Column 10, Lines 24-25 should read – ... *jujube* extract is present and is prepared by a method comprising the steps of: ...

Signed and Sealed this
Ninth Day of August, 2011

David J. Kappos
*Director of the United States Patent and Trademark Office*